US006106874A

United States Patent [19]

Liebrecht et al.

[11] Patent Number: 6,106,874

[45] Date of Patent: Aug. 22, 2000

[54] CALCIUM FORTIFIED JUICE-BASED NUTRITIONAL SUPPLEMENT AND PROCESS OF MAKING

[75] Inventors: Jeffery Wayne Liebrecht, Columbus; Kenneth Mark Phillips, Bexley, both of Ohio

[73] Assignee: Abbott Laboratories, Abbott Park, Ill.

[21] Appl. No.: 09/195,789

[22] Filed: Nov. 18, 1998

[51] Int. Cl.$^7$ ...................................................... A23L 1/304

[52] U.S. Cl. ............................ 426/74; 426/583; 426/599

[58] Field of Search ............................... 426/599, 74, 583

[56] References Cited

U.S. PATENT DOCUMENTS

| | | | |
|---|---|---|---|
| 3,922,375 | 11/1975 | Dalan et al . | |
| 3,949,098 | 4/1976 | Bangert . | |
| 3,958,017 | 5/1976 | Morse et al. . | |
| 4,309,417 | 1/1982 | Staples et al. . | |
| 4,486,413 | 12/1984 | Wiesenberger et al. . | |
| 4,722,847 | 2/1988 | Heckert . | |
| 4,737,367 | 4/1988 | Langer et al. . | |
| 4,738,856 | 4/1988 | Clark . | |
| 4,740,380 | 4/1988 | Melachouris et al. . | |
| 4,748,034 | 5/1988 | deRham . | |
| 4,786,510 | 11/1988 | Nakel et al. . | |
| 4,830,862 | 5/1989 | Braun et al. . | |
| 4,871,554 | 10/1989 | Kalala et al. . | |
| 4,873,112 | 10/1989 | Mitchell et al. | 426/599 |
| 4,992,282 | 2/1991 | Mechansho et al. . | |
| 5,141,758 | 8/1992 | Monte . | |
| 5,185,166 | 2/1993 | Nakagawa et al. | 426/74 |
| 5,225,221 | 7/1993 | Camden et al. . | |
| 5,322,702 | 6/1994 | Selinger et al. . | |
| 5,474,793 | 12/1995 | Meyer et al. . | |
| 5,597,595 | 1/1997 | DeWille et al. . | |
| 5,641,531 | 6/1997 | Liebrecht et al. . | |

FOREIGN PATENT DOCUMENTS

| | | |
|---|---|---|
| 0 486 425 B1 | 5/1997 | European Pat. Off. . |
| 291097 | 11/1914 | Germany . |
| 1024408 | 3/1966 | United Kingdom . |
| WO 93 12672 | 7/1993 | WIPO . |

OTHER PUBLICATIONS

Derwent Abstract No.; 95–271433/199636, Jul. 11, 1995.
Derwent Abstract No.; 93–378643/199348, Dec. 1, 1993.
Derwent Abstract No.; 92–201211/199225, Oct. 7, 1992.
Derwent Abstract No.; 91–358280/199149, Oct. 25, 1991.
Derwent Abstract No.; 83–32393K/198314, Mar. 30, 1983.
Derwent Abstract No.; 76–41959X/197622, May 18, 1976.
Lacprodan MM–0525 Product Brochure, Mar. 1977.

*Primary Examiner*—Helen Pratt
*Attorney, Agent, or Firm*—J. Michael Dixon

[57] ABSTRACT

This invention relates to a low pH nutritional beverage that utilizes pectin-free fruit juice as a major component and a source of calcium selected from natural milk mineral, calcium lactate gluconate and mixtures thereof. The beverage preferably also contains water soluble vitamins, flavors and carbohydrates. The use of a pectin-free and clarified pear juice in a preferred embodiment of the beverage provides a fat-free beverage with a substantially clear appearance and a light, refreshing mouthfeel. The beverage is preferably produced using a "cold water process" that results in excellent physical stability of the beverage over shelf life and the reduction of browning.

20 Claims, No Drawings

CALCIUM FORTIFIED JUICE-BASED NUTRITIONAL SUPPLEMENT AND PROCESS OF MAKING

TECHNICAL FIELD

This invention is directed to a clear, sediment-free, stabilizer-free, low pH (3.0–4.0) liquid nutritional beverage that provides high levels of iron, Vitamin C, and calcium in a matrix that has a refreshing fruit flavor, a thin texture, and a highly acceptable mouthfeel. The invention also relates to a specific process for the manufacture of the beverage. The beverage according to this invention may be carbonated to enhance certain sensory characteristics. Other aspects of this invention relate to methods of providing nutrition to a patient. Further aspects relate to methods of supplementing a patient's diet with additional nutrients such as calcium, Vitamin C or iron.

BACKGROUND OF THE INVENTION

Nutritional supplements differ generally from nutritionally complete liquid foods in that they are not intended to provide all of the nutritional requirements of a human, but instead are intended to supplement other, more conventional, sources of nutrition. Nutritional supplements can take the form of pills, capsules, food bars, powders, and ready-to-drink beverages. Modern consumers not only desire that their beverages be refreshing and tasty, they also desire some level of nutritional supplementation, especially for the important vitamins and minerals such as calcium, iron, Vitamin C, the B vitamins, and folic acid.

Parents of toddlers and children are especially sensitive to the nutritional needs of their offspring and understand that unfortified juice products and soft drinks fall short of the nutritional needs of the growing child. Parents are also aware that for children to consume a nutritionally beneficial beverage, it must taste good and have a refreshing character. The beverage industry has expended significant efforts over the last two decades in developing products that provide significant levels of important vitamins and minerals in a matrix that is clear, refreshing, juice-based, of low viscosity, and with good physical stability over shelf life.

Taste fatigue is a common problem in patients who are required to consume the conventional milk-based nutritional supplements on a regular basis. In addition, some patients, particularly children, young women, and the elderly, have aversions to "milky" or "milk-shake" type supplements. The beverage of this invention is a juice-based alternative to the primarily milk-based supplements currently available. The present invention represents an acceptable and refreshing means of supplementing energy, vitamins, and mineral intake in those patients who are tired of the milk-based alternatives. The beverage of this invention has a pleasing appearance, is essentially free of sediment (clear or transparent) and has pleasing organoleptic properties (a thin texture and good taste). This beverage also contains high levels of calcium and provides a means for supplementing calcium intake in individuals requiring such supplementation. These individuals include children, adult females, especially lactating and post menopausal females.

U.S. Pat. No. 5,641,531 to Liebrecht, et al., discloses a protein-containing nutritional supplement that is essentially devoid of added macronutrients and fat. This patent teaches that a clear, low viscosity beverage can be produced by: 1) preparing an acidified, aqueous solution of whey protein isolate at a pH of about 2.8 to about 3.3; 2) preparing an aqueous solution of carbohydrates; and 3) thereafter combining the two solutions. This patent does not suggest the use of a pectin-free and clarified fruit juice and a source of calcium selected from natural milk mineral, calcium lactate gluconate and mixtures thereof to prepare a clear, thin, and refreshing, nutritionally significant beverage.

EP Patent 486,425 to Sandoz Nutrition Ltd., discloses a liquid formulation comprising, based on the total formulation calories, from 40%–90% of the calories as carbohydrates, from 2%–30% of the calories as protein, from 0%–35% of the calories as fat and from 0%–17% of the calories as fiber wherein the protein source is at least 60% by weight whey protein concentrate and the pH of the formulation is from 3.5 to 3.9. This patent does not suggest the use of depectinized fruit juice to provide a juice-based product that can be easily flavored and that results in a substantially clear beverage that has excellent physical stability over shelf life.

U.S. Pat. No. 5,597,595 to DeWille, et al., discloses a liquid beverage consisting of water, calcium glycerophosphate as a source of calcium, a Vitamin D emulsion using a gum selected from gum arabic, gum tragacanth, and xanthan gum, wherein the beverage contains from 7.2%–18% calcium on a dry weight basis. This patent does not suggest or disclose the use of a natural milk mineral concentrate and/or calcium lactate gluconate as a source of highly bio-available calcium.

U.S. Pat. No. 5,322,702 to Selinger, et al., discloses an opacifying material of microgranular protein. This material is disclosed as being prepared by wet milling denatured whey protein isolate. This reference defines the terms "denatured whey protein isolate", "lactalbumin," and "isolate" as mixtures of water insoluble denatured dairy whey proteins. The denatured whey protein isolate typically has a dry weight lactose content of less than 20% and preferably less than 10%. This patent does not suggest that 0.5% to about 4.0% by weight of a whey protein isolate be combined with from 0.1% to 3.0% by weight of specific sources of calcium and a depectinized fruit juice to produce a clear, thin, and refreshing beverage.

U.S. Pat. No. 4,992,282 to Mehansho, et al., discloses vitamin- and mineral-fortified beverages that are stable and contain Vitamin A in the form of encapsulated beta carotene, Vitamin C, and riboflavin. The beverages according to this reference also contain at least 3% by weight fruit juice. The fruit juices disclosed include grape, pear, passion fruit, cherry, pineapple, banana, grapefruit, apple, cranberry, and mixtures thereof. This reference fails to suggest or disclose the use of a pectin-free and clarified fruit juice that provides a base for the production of a substantially clear beverage that utilizes a natural milk mineral and/or calcium lactate gluconate as a source of calcium.

U.S. Pat. No. 4,486,413 to Wisenberger, et al., discloses a protein-containing drink with a pH of 4.0 to 5.0 consisting essentially of 30–90 wt. % of a fruit juice or a mixture of fruit juices having a solids content of 4–20 wt. %; 2–20 wt. % of a whey concentrate corresponding to a whey protein content of 1.2–5 wt. % wherein the lactose content of the whey concentrate has been enzymatically cleaved; mineral salts and vitamins.

U.S. Pat. No. 4,309,417 to Staples discloses an isotonic beverage that contains from about 1% to about 3% by weight of a whey protein concentrate prepared by ultrafiltration. Most of the electrolytes provided in the beverage of this reference are supplied by the whey protein concentrate. The beverage of this patent is directed to electrolyte solutions that rapidly replace body fluids, electrolytes as well as protein that are lost during periods of strenuous physical activity.

U.S. Pat. No. 3,922,375 to Dalan, et al., discloses a process for preparing a soluble whey protein fraction that can be incorporated into beverages for protein enrichment purposes and can also be used as a constituent of a clouding agent.

U.S. Pat. No. 4,871,554 to Kalala, et al., is directed to a calcium-fortified beverage comprising water, concentrated fruit juice, and a solubilized calcium component consisting of tribasic calcium phosphate and calcium lactate. In similar fashion, U.S. Pat. No. 4,738,856 to Clark describes a beverage that uses a mixture of calcium ascorbate with calcium aspartate and/or calcium orotate as the source of bioavailable calcium.

U.S. Pat. No. 4,722,847 to Heckert discloses a calcium-supplemented single-strength fruit juice beverage that contains about 0.06% to about 0.26% by weight solubilized calcium, from about 0.4% to about 4% by weight of a mixture of citric acid and malic acid at weight ratios of from about 5:95 to about 90:10, respectively.

While the prior art beverages disclose the supplementation of juice-based drinks with calcium sources such as calcium glycerophosphate, calcium hydroxide, calcium carbonate ($CaCO_3$), calcium citrate-malate, calcium oxide ($CaO$), and the like, they have failed to appreciate that a natural milk mineral concentrate and/or calcium lactate gluconate, that is essentially free of protein and fat, would be useful in preparing a clear, thin, juice-based beverage. Further, the prior art has failed to realize the benefits associated with the use of a pectin-free and clarified juice as the base for preparing a clear, thin nutritional supplement. Further, the prior art has failed to solve the problems of browning, physical stability, and sediment formation that is associated with the typical vitamin and mineral fortified juice-based beverage. Most importantly, the prior art has suggested that stabilizers such as pectins and gums be used to reduce the formation of sediment and enhance physical stability problems. This is contrary to the present invention. One surprising aspect of the present invention is that a highly stable beverage can be prepared without the use of the typical pectins and gums. In fact, the beverage of the invention is essentially devoid of pectins and stabilizing gums. In view of the present disclosure or through the practice of the present invention, other advantages or solutions to other problems will become apparent.

SUMMARY OF THE INVENTION

A great deal of effort has been expended by the food industry in determining how to prepare fruit juice-based beverages containing supplemental calcium. The addition of calcium directly to fruit juice results in the precipitation of the calcium. To prevent the occurrence of this precipitation, a number of stabilizers have been developed that will keep the calcium in solution for extended periods of time. Such stabilizers include pectins and gums. While these stabilizers solve the precipitation problem, they create other problems that have adverse effects upon the palatability of these beverages.

These stabilizers cloud the beverage and make it impractical to prepare a clear beverage, that is preferred by a large number of consumers. The viscosity of the beverage is raised due to the presence of the stabilizer. The increased viscosity results in a thick texture, reminiscent of a milk shake, rather than a juice. Such a texture is undesirable to a large number of consumers.

Further efforts in the food industry have focused on incorporating proteins into fruit juice-based beverages. These efforts led to the discovery that it was possible to prepare clear, low pH beverages by utilizing whey protein concentrate. However, these same efforts lead to the conclusion that it was not possible to add supplemental calcium to such beverages without sacrificing clarity . These same efforts also led to the conclusion that it was inevitable that supplemental calcium would result in sedimentation and a thick texture in such clear beverages In accordance with the present invention, it has been discovered how to prepare calcium supplemented fruit juice-based beverages without using stabilizers such as pectins, gums or oils. Such beverages are clear and will remain clear during the course of their normal shelf lives of approximately one year. Further it has been discovered how to prepare clear fruit juice-based beverages containing both supplemental calcium and whey protein concentrate that have similar properties of clarity.

It has been discovered that the use of natural milk mineral concentrate or calcium lactate gluconate will solve the problems described above. Calcium supplemented fruit juice-based beverages prepared with either natural milk mineral concentrate or calcium lactate gluconate do not require the presence of a stabilizer. Further whey protein concentrate can be incorporated into such beverages without negatively impacting the clarity of such beverages. Additionally it has been discovered that these sources of calcium do not interact with other ingredients, as other sources of calcium typically do in liquid media.

DETAILED DESCRIPTION OF THE INVENTION

The present invention discloses a beverage containing supplemental calcium and a method for preparing such a beverage. The beverage may be in a ready-to-drink form (single strength), a concentrate or a powder. Other aspects of the invention are directed to a method for providing calcium supplementation to a patient, as well as providing nutrition to such a patient.

The beverage of the present invention in single-strength or ready-to-drink form, in its broadest terms, comprises: a) water; b) from about 5% to about 95% by weight depectinized fruit juice; and c) from about 0. 1% to about 3.0% by weight of a source of calcium selected from natural milk mineral, calcium lactate gluconate or mixtures thereof. Preferably, the depectinized fruit juice is a clarified fruit juice so as to limit browning of the product during manufacture and storage.

The beverages according to the invention may also optionally contain one or more of the following ingredients: a) water soluble vitamins such as pantothenic acid, biotin, Vitamin $B_{12}$, folic acid, Vitamin $B_6$, niacin, Vitamin $B_2$, Vitamin $B_1$ and bioavailable iron; b) a supplemental source of carbohydrate (beyond that provided by the depectinized fruit juice); c) from about 0.5% to about 4% by weight of a whey protein isolate; d) from about 0.3% to about 1.0% by weight of an edible acid; e) from about 0.1% to about 1.5% by weight of flavoring agent; and/or 6) from about 0.05% to about 0.5% by weight ascorbic acid. The pH of the beverage is in the range of from about 3.0 to about 4.0, with a pH of 3.2 to 3.8 being more preferred and a pH of 3.4 to 3.6 being most preferred.

There is also disclosed a ready-to-drink nutritional beverage comprising:

a) water;

b) from about 25% to about 45% by weight of a single-strength depectinized fruit juice selected from the citrus juices, non-citrus juices or mixtures thereof;

c) from about 0.2% to about 2.5% by weight of a source of calcium selected from natural milk mineral, calcium lactate gluconate or mixtures thereof;

d) at least one element selected from the group consisting of pantothenic acid, biotin, Vitamin $B_{12}$, folic acid, Vitamin $B_6$, niacin, Vitamin $B_2$, Vitamin $B_1$ and a source of bioavailable iron;

e) a total carbohydrate content of at least about 30 grams up to about 260 grams per liter;

f) from about 0.5% to about 2.0% by weight of a whey protein isolate;

g) from about 0.3% to about 1.0% by weight of at least one edible acid, and;

h) from 0.05% to about 0.5% by weight ascorbic acid.

As used herein, the term "beverage" refers to a liquid composition that is in a single-strength, ready-to-serve, drinkable form. The terms "beverage," "juice-based beverage," "nutritional supplement," "low pH juice-based beverage," "nutritional beverage," etc., are being used interchangeably within this document. As used herein the term "single strength" refers to the brix standards of identity for any given juice. As used herein, the term "comprising" or "comprises" means various components can be conjointly employed in beverages and concentrates of the present invention. Accordingly, the more restrictive terms "consisting essentially of" and "consisting of" are embodied in the term "comprising."

The beverages of this invention will typically contain water. The quantity of water that is utilized may vary depending on whether the beverage is in a ready-to-drink form, a concentrate form, a powdered form suitable for reconstitution, a frozen puree, etc. However, for the ready-to-drink beverage the quantity of water will typically vary from about 2% to about 95% by weight water. More preferably the amount of water utilized will vary from about 40% to about 80% by weight water and most preferably will be about 55% to 75% by weight. The type of water is not critical. It may be ordinary tap water, distilled water, purified water, etc. Depending on the preference of the consumer, the water may be carbonated if desired.

The term "depectinized fruit juice," as used here and in the claims, means a fruit juice that has had most of the pectins removed (depectinized) through processes such as enzymatic digestion. The removal of the pectins may also be accomplished through techniques such as chromatography, precipitation, or any other technique now known or later developed. The term "depectinized juice" has a well-known meaning to those skilled in the art. Typically though, a juice in which the pectin content is no greater than about 0.25 wt. % and more preferably about 0.05 wt. %, or less, is thought of as being "depictinized fruit juice" within the industry. The depectinized fruit juice may also be filtered to be essentially clear.

Fruit juices useful in the inventive beverage include citrus juices and non-citrus juices. The citrus juices include juices from orange, lemon, lime, grapefruit, tangerine, and mixtures thereof. The non-citrus juices can be obtained from apple, grape, pear, cherry, berry, pineapple, peach, apricot, plum, prune, passion fruit, banana, and mixtures thereof. The preferred juices for use in this invention are depectinized and clarified pear juice, apple juice and white grape juice as they are inexpensive, are clear, are colorless, and have a mild flavor that can be overwhelmed by artificial and natural flavors, such as cherry and orange.

The quantity of depectinized fruit juice that may be utilized in the preparation of the beverages of the invention can vary widely. Typically however, the depictinized fruit juice will be present in a quantity of from about 5% to about 95% by weight, more preferably from about 20% to about 60% by weight, and most preferably from about 25% to about 45% by weight.

Representative of a depectinized fruit juice useful in this invention is a clarified pear juice concentrate available from SVZ International, B.V. of Etten-Lear, Holland. This product is a concentrate, made of mature pears (*Pyrus communis*) that has been depectinized, filtered, concentrated, and pasteurized. This pear juice has a Brix of 67.5°–68.5°(as a concentrate), a pH of 3.2 to 3.8, a Brix at single strength of about 11.5° and no detectable pectin (i.e., about 0.05 wt. % or less).

The Brix scale is a hydrometer scale for sugar solutions so graduated that its readings at a specified temperature represent percentages by weight of sugar in the solution. Brix levels for single strength and concentrates of fruit juices are specified by law in many countries. For example, in the U.S.A., a single-strength pear juice must have a Brix of at least 8.0°, while in Europe, a single-strength pear juice must have a Brix of at least 11.9°. All amounts of fruit juice referred to herein are on a single-strength basis unless specified otherwise (as relevant for the particular country or region). The ready-to-drink beverages of this invention will have a sugar content of from about 2°–35° Brix, preferably from 4°–25° Brix and most preferably from 6°–16° Brix.

All of the beverages of this invention contain supplemental calcium. As noted above, it has been discovered that natural milk mineral and/or calcium lactate gluconate can be used to produce calcium supplemented fruit juice-based beverages without the use of stabilizer. Such beverages have the advantage of being clear, even in the presence of whey protein. Any reference to an amount of calcium in this application is referring to the amount of the calcium salt (i.e., the amount of natural milk mineral concentrate or calcium lactate gluconate) and not to the amount elemental amount of calcium within the salt. However typically, the beverages will contain from about 0.1% to about 3.0% by weight of either of the calcium sources described above. As is well known to those skilled in the art, the quantity will be varied to meet the nutritional requirements of the patient class for whom the beverage is intended. If the beverage is intended for a pediatric population it will contain from about 0.3 wt. % to about 1.5 wt. % of the calcium source and more preferably about 0.3 wt. % to about 1.3 wt. % of the calcium source. If the beverage is intended for an adult population then the quantity will vary from about 0.3 wt. % to about 2.0 wt. % and more preferably about 0.5 wt. % to about 1.6 wt. %.

As used herein, the term "natural milk mineral" refers to an isolate from mammalian milk that comprises a high concentration of minerals, especially calcium. The natural milk mineral is typically produced using ultrafiltration technology and is a waste stream from whey protein isolate production. A representative natural milk mineral is available from MD Foods Ingredients amba of Denmark under the name Lacprodan MM-0525. This product starts with whey that is subjected to ultrafiltration to remove the protein. The ultrafiltration permeate is then heated to create a precipitate. The precipitate is then separated, pasteurized, and then spray dried. Another source of highly bioavailable calcium useful in the present invention is a mixture of calcium lactate and calcium gluconate available from Glucona B.V. of The Netherlands under the name Gluconal CAL. It is a mixture of $C_{12}H_{22}O_{14}Ca$ (mol. wt. 430.4) and $C_6H10_6Ca$ (mol. wt. 218.2) and is about 10%–11% Ca by weight. In general, gluconates are found in products such as toothpaste, clothes, medicines, cosmetics, paper soap, cleaning supplies, and food. Gluconates are obtained by the fermentation of glucose and operate as carriers for minerals, acidifiers, and chelating agents.

With respect to the source of calcium for the inventive beverage, it has been determined that the use of conventional calcium sources such as calcium hydroxide, calcium glycerophosphate, calcium lactate-malate, and the like are detrimental to the production of a clear, thin beverage. Therefore, it has been determined that the use of natural milk mineral such as Lacprodan® MM-0525 from MD Foods Ingredients amba, Denmark is effective in producing the inventive beverage that contains high levels of bioavailable calcium. Lacprodan® MM-0525 has the following chemical composition (% by weight):

| | |
|---|---|
| Protein | 4% max. |
| Fat | 1% max. |
| Lactose | 15% max. |
| Minerals | 70% max. |
| Moisture | 6% max. |

The mineral distribution for this product is as follows (% by weight):

| | |
|---|---|
| Sodium | approx. 1% |
| Potassium | approx. 1.5% |
| Calcium | 25% min. |
| Magnesium | approx. 0.5% |
| Phosphorus | 11% min. |
| Chloride | approx. 2% |

Lacprodan® MM-0525 as a 10% by weight solution in water has a pH of 6.6–7.3 and the color in solution at a pH of 4 or less is clear.

As noted above, the beverages of this invention may optionally contain whey protein isolate. Such beverages have the advantage of supplying amino acids to the patient as well as calcium. The quantity of whey protein isolate that is utilized can vary widely. Typically these beverages will contain from about 0.5% to about 4% by weight of a whey protein isolate, more typically from about 0.5% to 2% by weight, and more typically about 1%.

The whey protein isolate useful in this invention can be supplied by numerous commercial sources. Whey protein isolate is greater than 90% protein by weight and contains very low levels of fat and lactose. Commercially available sources of whey protein isolate that are useful in the present invention are Alacen® 895 from New Zealand Milk Products, Inc., of Santa Rosa, Calif.; Provon-190 from Avonmoor Ingredients, Inc., of Monroe, Wisc., and Lacprodan® from MD Foods Ingredients amba, Denmark. Typically, the inventive beverage has whey protein isolate present in the range from about 0.7% to about 1.0% by weight.

In addition to the carbohydrate inherently present in the fruit juice, additional quantities of supplemental carbohydrates may be optionally added to the beverage, depending upon the patient population the beverage is being designed for. For example, if the beverage is to be used in a pediatric population, then glucose is typically added to sweeten the taste. Such variations are well known to those skilled in the art and such manipulations are intended to be covered by this invention.

The quantity of any supplemental carbohydrate can vary widely. However typically, the fruit juice will contribute at least about 30 grams of carbohydrate per liter and more typically from 30 to 120 grams per liter. It is preferred that the total carbohydrate content of the beverages from both the juice and supplemental carbohydrates be no greater than about 260 grams per liter and more preferably no greater than 135 grams per liter. Any supplemental carbohydrates will typically be added in a quantity of from about 15 to about 90 grams per liter.

The carbohydrate may be any carbohydrate source appropriate for use in nutritional beverages. The carbohydrate component of the formulation may be any nutritionally acceptable blend of carbohydrates such as sucrose, glucose, fructose, corn syrup solids and maltodextrin. Artificial sweeteners such as saccharin and aspartame may also be used to enhance the organoleptic quality of the formulation.

The fat content of the inventive beverage is essentially zero. There is no fat component to this invention other than the fat content inherent to the raw materials, such as the whey protein. Therefore, the product of the invention is essentially devoid of added fat. As used herein the term 'devoid of fat' means a concentration of fat that is less than or equal to 0.50 weight percent.

As noted above, the pH of the beverages of this invention should range from about 3.0 to about 4.0. This pH range can be obtained by the addition of food grade acids such as hydrochloric acid, malic acid, citric acid, phosphoric acid or mixtures thereof. Any food grade acid known in the art may be utilized. The preferred acid to modify the pH of the beverage is phosphoric acid.

The acid inherently provided by the depectinized fruit juice will also effect the pH level of the finished product. As the relative level of fruit juice is increased, a corresponding decrease in the amount of food grade acid required to adjust the pH of the beverage is observed. It is also preferred for the beverages of this invention to contain high levels of Vitamin C. The presence of Vitamin C (ascorbic acid) will also serve to lower the pH of the beverage. The quantity of ascorbic acid utilized will typically range from about 0.05% to about 0.1% by weight. The quantity of food grade acid utilized will vary with the relative concentration of depectinized fruit juice and Vitamin C in the beverage. Manipulating the concentration of food grade acid to obtain a pH in the range of from about 3.0 to about 4.0 is well known to those skilled in the art. Typically, the beverage will contain at least about 0.5 weight percent of a food grade acid and no more than about 1 weight percent of such acid.

An additional aspect of the invention relates to simultaneously achieving a clear, thin, juice-based beverage that contains vitamins. Those skilled in the nutritional arts will readily appreciate what materials can be used to accomplish the vitamin fortification. Representative of the vitamins useful in the present invention are ferrous sulfate, niacinamide, D-calcium pantothenate, pyridoxine hydrochloride, riboflavin, thiamin mononitrate, folic acid, biotin and cyanocobalamin. The beverage of the present invention may also be supplemented with the amino acid taurine. Typically the beverages will be formulated to supply from about 25% to about 100% of the RDI for all water soluble vitamins, i.e., (Vitamin C, thiamin, riboflavin, niacin, Vitamin $B_6$, folate and Vitamin $B_{12}$) in a single serving. A single serving is the amount one can consume in one sitting. This quantity can vary widely but will typically comprise from 50–400 ml, more typically about 240 ml (or at least 3%–4% of the USRDI per fluid oz.).

One important embodiment of the present inventive beverage is a drink that contains at least 25%, more preferably at least 33%, of the United States Recommended Daily Intake (USRDI), as established by the U.S. Food & Drug Administration, for calcium and optionally iron in a 240 ml serving (this may be alternatively expressed as about 3% to about 4% of the RDI per fluid oz.). There are well-recognized problems associated with adding such high levels of iron and calcium to foods and beverages. For example, most calcium supplements tend to be rather insoluble or tend to have a "chalky" taste or mouthfeel. Iron supplements tend to discolor foodstuffs, or to be organoleptically unsuitable. Moreover, it is particularly difficult to formulate foods, and especially beverages, containing mixtures of calcium supplements and iron supplements, inasmuch as these minerals tend to interact. This interaction not only affects the organoleptic and aesthetic properties of the foods and beverages, but also undesirably affects the nutritional bioavailability of these minerals themselves. The present invention, in part, is based upon the discovery that the use of natural milk mineral and/or calcium lactate gluconate as the source of calcium allows for the supplementation of the beverage with high levels of calcium and iron without significant detrimental impact. Preferably, the iron is in the ferrous (iron II) state, however, ferric iron (iron III) is also acceptable. The ferrous iron is better tolerated and more efficiently utilized by the body than the ferric iron. The preferred form of iron is ferrous sulfate.

An additional aspect of the present invention relates to the beverage's thin texture and light mouthfeel. It has been determined that to achieve the goals of thin texture and good mouthfeel, the viscosity of the product should be less than about 15 cP, preferably less than 10 cP and most preferably between 4 and 5 cP, as determined by a Brookfield Viscometer at 22° C. using a #1 spindle at 60 rpm.

It has been determined that to achieve the beverage's clear appearance, thin texture and low viscosity, the addition of stabilizers should be avoided. Conventional stabilizers have been found to cloud the beverage, detrimentally impact mouthfeel and react with flavors. In fact, the presence of naturally occurring stabilizers such as pectin in the fruit juice should be avoided. This approach is contrary to conventional wisdom that suggests that when high levels of calcium are added to a beverage, a stabilizer should also be used. The prior art teaches that pectins, algins, hydrolyzed starches, xanthan gum and other edible gums be added or be present in the juices that are utilized. Therefore, one aspect of the present invention resides in the use of a depectinized fruit juice in combination with natural milk mineral and/or calcium lactate gluconate to produce a beverage with high levels of calcium and a light, clean tasting character that is essentially clear in appearance.

Further, in a yet more preferred embodiment, the beverage according to the invention uses depectinized and clarified pear juice, apple juice, white grape juice and mixtures thereof. These base juices are especially preferred as they have a bland flavor that is easily masked with other natural and/or artificial flavors such as strawberry, cherry, orange and the like.

One method that may be used to produce the beverage of the present invention has been designated "the cold water process." In the cold water process, neither the raw materials nor the premixes are heated above about room temperature until just prior to packaging. At the point of packaging, the beverage is heated using conventional equipment and technology so as to assure sterility over the shelf life of the product. Other than manipulating temperature, the nutritional products of this invention may be manufactured using techniques known to those skilled in the art. Generally speaking, cold water is added to a tank followed by the calcium source. This solution is agitated until the calcium is dissolved. Any whey protein isolate, supplemental carbohydrates, etc., are added sequentially with agitation to allow their dissolution. The depectinized fruit juice is then added followed by any vitamins. The pH is then adjusted as necessary with a food grade acid. The resulting mixture is optionally flavored and the liquid terminally sterilized or dried to produce a powder. The beverage can be sterilized and subsequently utilized on a ready-to-feed (RTF) basis or stored in a concentrated liquid or a powder form. As noted above, during processing the beverage should be kept at approximately room temperature or below prior to its final terminal sterilization. A more detailed description of the manufacturing procedure follows in Example I. The invention also includes a nutritional supplement beverage produced in accordance with the method described herein. Any reference herein to a numerical range or numerical quantity should be interpreted as referring to the range specified therein and to any subset encompassed within the stated range. For example, a range of 1–10 should be interpreted as providing support for a range of 3–5, 1–9, 2–10, 4–5, 7–8,5,6,7, etc.

The beverage according to the invention can be prepared with the following ranges of properties and components:

| | RANGE PER 240 ML SERVING | |
|---|---|---|
| ITEM | GENERAL | PREFERRED |
| Energy (kcal) | 90–150 | 110–120 |
| Protein (gm) | 0.5–4.0 | 1.0–3.0 |
| Carbohydrate (g) | 15–40 | 20–30 |
| Fat (g) | 0–1.0 | 0–.25 |
| Calcium (mg)/elemental | 200–350 | 250–275 |
| Iron (mg) | 2.0–4.5 | 2.8–3.8 |
| Taurine (mg) | 0–20 | 7–17 |
| Vitamin C (mg) | 20–60 | 35–45 |
| Vitamin B1 (mg) | 0–.4 | .1–.3 |
| Vitamin B2 (mg) | 0–.4 | .1–.3 |
| Niacin (mg) | 0–.4 | 2.5–3.5 |
| Vitamin B6 (mg) | 0–.5 | .25–.35 |
| Folic Acid (mcg) | 0–20 | 13–18 |
| Vitamin B12 (mcg) | 0–.4 | .2–.3 |
| Biotin (mcg) | 0–.8 | 5–7 |
| Pantothenic Acid (mg) | 0–2.0 | .5–1.5 |

The beverage according to the invention would be especially beneficial for toddlers/children of 1–10 years of age. Various modifications of components, such as the number and type of carbohydrates, can be made without departing from the fundamental discovery that use of a depectinized fruit juice and a source of calcium selected from natural milk mineral, calcium lactate gluconate and mixtures thereof, can produce a physically stable and refreshing nutritional beverage.

DETAILED DESCRIPTION OF THE PREFERRED EMBODIMENTS

In accordance with the foregoing summary of the invention, the following Example I is one embodiment of the beverage of the present invention and a method of its production. For making a large quantity of the nutritional supplement in accordance with the present invention, the following bill of materials was utilized.

| Bill of Materials | |
|---|---|
| Ingredient | Per 1 kg |
| Water | 861.53 g |
| Concentrated Pear Juice | 52.50 g |
| Sucrose | 34.78 g |
| Fructose | 24.41 g |
| Whey Protein Isolate | 8.73 g |
| Glucose | 6.44 g |
| Phosphoric Acid | 5.0 g |
| Natural Milk Mineral | 4.23 g |
| Natural Flavors | 1.5 g |
| Ascorbic Acid | .625 g |
| Water Soluble Vitamin Premix | .238 g |
| Maltodextrin (DE10) | |
| Ferrous Sulfate | |
| D-Ca Pantothenate | |
| Pyridoxine HC1 | |
| Riboflavin | |
| Thiamin Mononitrate | |
| Folic Acid | |
| Biotin | |
| Cyanocobalamin | |
| Taurine | |

EXAMPLE I

Production of Beverage Containing Natural Milk Mineral

Nine 473 liter (125 gallon) batches were manufactured using the process described below. In the first step, the appropriate amount of cold water (less than 10° C., 50° F.) was added to a blend tank and the natural milk mineral was then added. Mixing occurred until the natural milk mineral was dissolved. The whey protein isolate was then added to the tank and agitation continued until the whey protein isolate dissolved. The carbohydrate system was then added and agitated until it dissolved. The pear juice concentrate was added and blending continued. The pH of the solution was adjusted to 3.35–3.65 with 85% phosphoric acid. The water soluble vitamin premix and flavor was then added with continued agitation. This mixture was then pumped to a finish product tank and ratio testing was performed. The solution was standardized with water and ascorbic acid. The beverage was then aseptically processed (tubular heat exchangers) and filled into 250 ml low density polyethylene juice boxes.

The boxes were stored at room temperature for 30 days and then biological testing was conducted. All biological testing was negative, therefore indicating a sterile product. Physical stability, color and flavor were all acceptable.

After two months of storage, tops of the containers were removed and viewed for any signs of yeast and mold growth. All containers inspected were rated as clean/clear. No changes in pH, viscosity or density were noted at this time. Product flavor was found to be acceptable.

After six months of storage, physical stability, pH, viscosity and density remained acceptable. Flavor was found to be acceptable except for the apple samples, as a slight mentholyptus note was detected.

The beverage of the present invention can be made in a ready-to-consume form, in the form of a concentrate, a frozen sorbet or powder form and may be flavored with natural and/or artificial flavors. The beverage of this invention may also be carbonated. The nutritional beverage of the present invention, due to its thinness and clarity, has been found to produce a refreshing, tart, juice-like mouthfeel. The nutritional beverage of the present invention may be packaged in accordance with materials and methods used in the packaging art.

Industrial Applicability

Some patients in need of nutritional supplementation simply do not like or cannot tolerate milk-based supplements. These patients may also suffer from taste fatigue that can hinder compliance. The product of this invention will offer malnourished patients in need of calcium and/or iron supplementation a new supplement that will improve intake and thereby improve nutritional status. The product of this invention provides a high level of nutritional value in a clear juice-like beverage that will be found useful in the medical community.

In accordance with the foregoing disclosure, it will be within the ability of one skilled in the relevant arts to make modifications to the present invention, such as through the substitution of equivalent materials and/or their amounts, without departing from the spirit of the invention as reflected in the appended claims.

We claim:

1. A thin, ready-to-drink nutritional beverage comprising:

a) water;

b) from about 5 to about 95% by weight of single strength depectinized fruit juice;

c) from about 0.1 to about 3.0% by weight of a supplemental source of calcium selected from the group consisting of natural milk mineral, calcium lactate gluconate and mixtures thereof;

d) at least about 0.5% by weight of a whey protein isolate, and;

e) said beverage is clear and has a viscosity of less than about 15 centapoise.

2. The nutritional beverage according to claim 1 in which said water is present in an amount of from about 2% to about 95% by weight.

3. The nutritional beverage according to claim 2 in which said depectinized fruit juice is present in an amount of from about 20% to about 60% by weight.

4. The nutritional beverage according to claim 3 in which said calcium source is present in an amount of from about 0.2% to about 2.5% by weight.

5. The nutritional beverage according to claim 2 in which said depectinized fruit juice is present in an amount of from about 25% to about 45% by weight.

6. The nutritional beverage according to claim 4 in which said calcium is present in an amount of from about 0.3% to about 0.6% by weight.

7. The nutritional beverage according to claim 6 wherein said source of calcium is natural milk mineral.

8. The nutritional beverage according to any one of claims 2–6 or 7 which additionally comprises at least one nutrient selected from the group consisting of: Pantothenic acid, biotin, Vitamin $B_{12}$, folic acid, Vitamin $B_6$, niacin, Vitamin $B_2$, Vitamin $B_1$ and a source of bioavailable iron.

9. The nutritional beverage according to any one of claims 2–6 or 7 which contains a sufficient amount of an edible acid, so that said beverage has a pH in the range of from about 3.0 to about 4.0.

10. The nutritional beverage according to claim 7 in which the beverage further comprises from about 0.3% to about 1% by weight of an edible acid.

11. The nutritional beverage according to claim 10 which further comprises from about 0.5% to about 3% by weight of a whey protein isolate.

12. The nutritional beverage according to claim 7 which further contains from about 0.05% to about 0.5% by weight of ascorbic acid and wherein said nutritional beverage has a pH in the range of from about 3.2 to about 3.8.

13. The nutritional beverage according to claim 7 which further contains from about 0.5% to about 2% by weight of a whey protein isolate.

14. A method for providing nutrition to a patient comprising administering to a patient in need thereof a sufficient amount of a nutritional beverage according to claim 1.

15. Add A method for providing calcium supplementation comprising administering to a patient in need thereof a sufficient amount of a nutritional beverage according to claim 1.

16. The beverage according to claim 1 wherein said beverage is in the form of a concentrate, a powder or a frozen sorbet.

17. The nutritional beverage according to claim 1 having a viscosity of less than about 10 centipoise.

18. A thin ready-to-drink nutritional beverage comprising:

a) water;

b) from about 20 to about 50% by weight of a single strength depectinized fruit juice selected from the group consisting of citrus juices, non-citrus juices and mixtures thereof;

c) from about 0.1 to about 3.0% by weight of a source of calcium selected from the group consisting of natural milk mineral, calcium lactate gluconate and mixtures thereof;

d) at least one element selected from the group consisting of pantothenic acid, biotin, vitamin $B_{12}$, folic acid, vitaminm $B_6$, niacin, vitamin $B_2$, vitamin $B_1$ and a source of bioavailable iron;

e) from about 0.5 to about 2.0% by weight of a whey protein isolate;

f) from about 0.8 to about 1.0% by weight of at least one edible acid; and additionally g) from about 0.05to about 0.5% by weight ascorbic acid;

h) a total carbohydrate content of at least about 30 grams, and up to about 260 grams per liter, and;

i) said beverage is clear and has a viscosty of less than about 15 centipoise.

19. The nutritional beverage according to claim 18 having a viscosity of less than about 15 centipoise.

20. A process for producing a thin ready-to-drink nutritional beverage containing:

a) water;

b) from about 20 to about 50% by weight of a single strength depectinized fruit juice selected from the citrus juices, non-citrus juices or mixtures thereof;

c) from about 0.1 to about 3.0% by weight of a supplemental source of calcium selected from natural milk mineral, calcium lactate gluconate or mixtures thereof;

d) at least one element selected from the group consisting of pantothenic acid, biotin, vitamin $B_{12}$, folic acid, vitamin $B_6$, niacin, vitamin $B_2$, vitamin $B_1$ and a source of bioavailable iron;

e) from about 0.5 to about 2.0% by weight of a whey protein isolate;

f) from about 0.3 to about 1.0% by weight of at least one edible acid and additionally;

g) from 0.05 to about 0.5% by weight ascorbic acid, and h) a total carbohydrate content of at least about 30 grams up to about 260 grams per liter comprising the steps of:

a) placing said water in a blend tank and maintaining at a temperature of less than 22° C. through steps a) through h);

b) adding said source of calcium to said blend tank and mixing until said source of calcium is dissolved;

c) adding said whey protein isolate to the solution of step b) and mixing until said whey protein isolate is dissolved;

d) adding said carbohydrate to the solution of step c) and mixing until said carbohydrate is dissolved;

e) adding said depectinized fruit juice to the solution of step d);

f) adding said edible acid to the solution of step e) until a pH of less than 4.0 is achieved;

g) optionally adding at least one water soluble vitamin and at least one flavor to the solution of step f) and mixing and additionally;

h) adding ascorbic acid to the solution of step g) and mixing;

i) heating the solution of step h) to achieve sterility; and j) optionally packaging the solution of step i) into an appropriate package.

* * * * *

UNITED STATES PATENT AND TRADEMARK OFFICE

CERTIFICATE OF CORRECTION

PATENT NO. : 6,106,874
DATED : August 22, 2000
INVENTOR(S) : Jeffery Wayne Liebrecht, Kenneth Mark Phillips It is certified that error appears in the above-identified patent and that said Letters Patent is hereby corrected as shown below:

Claims,
Claim 18, part (f) should read: from about 0.3 to about 1.0% by weight of at least one edible acid; and additionally.

Signed and Sealed this

Ninth Day of October, 2001

*Attest:*

Nicholas P. Godici

NICHOLAS P. GODICI

*Attesting Officer* *Acting Director of the United States Patent and Trademark Office*